(12) United States Patent
Kaufman et al.

(10) Patent No.: US 8,460,619 B2
(45) Date of Patent: Jun. 11, 2013

(54) MICROFLUIDIC APPARATUS AND METHOD FOR PREPARING CYTOLOGICAL SPECIMENS

(75) Inventors: Howard B. Kaufman, Newton, MA (US); Tuan Ha, Randolph, MA (US)

(73) Assignee: CYTYC Corporation, Marlborough, MA (US)

( * ) Notice: Subject to any disclaimer, the term of this patent is extended or adjusted under 35 U.S.C. 154(b) by 476 days.

(21) Appl. No.: 12/574,554

(22) Filed: Oct. 6, 2009

(65) Prior Publication Data

US 2010/0093016 A1 Apr. 15, 2010

Related U.S. Application Data

(60) Provisional application No. 61/104,632, filed on Oct. 10, 2008.

(51) Int. Cl.
*A61B 10/00* (2006.01)
(52) U.S. Cl.
USPC ........... 422/536; 422/500; 422/501; 422/502; 422/503; 422/422; 422/50; 422/421
(58) Field of Classification Search
USPC .......................... 422/500–503, 422, 50, 421
See application file for complete search history.

(56) References Cited

U.S. PATENT DOCUMENTS

| 5,143,627 | A | 9/1992 | Lapidus et al. |
| 5,364,597 | A | 11/1994 | Polk, Jr. et al. |
| 5,503,802 | A | 4/1996 | Polk, Jr. et al. |
| 5,772,818 | A | 6/1998 | Polk, Jr. et al. |
| 5,942,700 | A | 8/1999 | Radcliffe et al. |
| 6,010,909 | A | 1/2000 | Lapidus |
| 6,225,125 | B1 | 5/2001 | Lapidus |
| 6,318,190 | B1 | 11/2001 | Radcliffe et al. |
| 6,562,299 | B1 | 5/2003 | Ostgaard et al. |

(Continued)

FOREIGN PATENT DOCUMENTS

| AU | 2007201766 | 5/2007 |
| JP | 3071426 | 9/2000 |

(Continued)

OTHER PUBLICATIONS

PCT International Search Report and Written Opinion for PCT/US2009/059724, Applicant CYTYC Corporation, Forms PCT/ISA/210, 220, and 237 dated Jan. 22, 2010 (13 pages).

(Continued)

*Primary Examiner* — Jyoti Nagpaul
(74) *Attorney, Agent, or Firm* — Vista IP Law Group LLP

(57) ABSTRACT

An apparatus for processing a specimen from a fluid sample includes a first set of one or more microfluidic channels configured to deliver the sample fluid to a filter disposed on an inflatable bladder configured to transfer the specimen from the filter to a slide. The apparatus is configured to collect an approximate monolayer of particles and includes a second set of one or more microfluidic channels configured to remove fluid flowing through the filter disposed on the inflatable bladder. The apparatus also includes a pressure source, a sample container connected to the pressure source and the first set of one or more microfluidic channels, a fluid flow gauge configured to measure a fluid flow rate through the filter, and a stain source connected to the first set of one or more microfluidic channels.

15 Claims, 5 Drawing Sheets

U.S. PATENT DOCUMENTS

| | | | |
|---|---|---|---|
| 6,572,824 B1 | 6/2003 | Ostgaard et al. | |
| 6,634,244 B2 | 10/2003 | Radcliffe et al. | |
| 7,223,363 B2 * | 5/2007 | McNeely et al. | 422/417 |
| 8,215,338 B2 | 7/2012 | Delattre et al. | |
| 2002/0160518 A1 * | 10/2002 | Hayenga et al. | 436/70 |
| 2002/0192701 A1 * | 12/2002 | Adey | 435/6 |
| 2006/0051250 A1 * | 3/2006 | Gonzalez et al. | 422/102 |

FOREIGN PATENT DOCUMENTS

| | | |
|---|---|---|
| WO | 02072264 | 9/2002 |
| WO | 03015923 | 2/2003 |
| WO | W003/036267 A2 | 5/2003 |
| WO | 2005016532 | 2/2005 |
| WO | W02007/082302 A2 | 7/2007 |
| WO | 2008077007 | 6/2008 |

OTHER PUBLICATIONS

Notice of Rejection for related application No. JP 2011-53119, Dispatch No. 053478, dated Jan. 29, 2013, including the translation of the Notice of Rejection provided by the foreign associate. (4 pages).

Notification of the First Office Action mailed Sep. 10, 2012, for related application CN 200980140057.9, applicant Cytyc Corporation, filed Oct. 6, 2009, including the translation provided by the foreign associate. (11 pages).

* cited by examiner

MICROFLUIDIC APPARATUS AND METHOD FOR PREPARING CYTOLOGICAL SPECIMENS

FIELD OF THE INVENTION

The disclosed inventions pertain to microfluidic apparatuses and methods for preparing specimens for microscopic examination, and more particularly to microfluidic apparatuses and methods for collecting particles suspended in a sample fluid and transferring the collected particles to a slide for microscope examination.

BACKGROUND

Many medical tests, including Papanicolaou (Pap) smears, require a physician to collect cells by brushing and/or scraping a skin or mucous membrane in a target area with an instrument. The cells are then smeared onto a slide, and are fixed and transported to a laboratory where the slide is stained. The slide can then be examined under a microscope by a cytotechnologist and/or a pathologist to identify cellular abnormalities. During evaluation, a pathologist may employ a polychrome technique, characterized by staining the nuclear part of the cells, to determine the presence of dysplasia or neoplasia. The pathologist may also apply a counter-stain for viewing the cytoplasm of the cells. Because the sample may contain debris, blood, mucus, and other obscuring artifacts, the test may be difficult to evaluate, and may not provide an accurate diagnostic assessment of the collected sample.

Cytology based on the collection of the exfoliated cells into a liquid preservative offers many advantages over the traditional method of smearing the cells directly onto the slide. A slide can be prepared from the cell suspension using a filter transfer technique, such as the Cytospin® technique and the Thin-prep® technique, as disclosed in U.S. Pat. Nos. 6,634,244, 6,572,824, 6,562,299, 6,318,190, 6,225,125, 6,010,909, 5,942,700, 5,772,818, 5,503,802, 5,364,597, and 5,143,627, which are expressly incorporated herein by reference for all that they teach and disclose.

Filter transfer methods generally start with a collection of cells suspended in a liquid. These cells may be collected and dispersed into a liquid preservative or they may naturally exist in a collected biological liquid. Dispersion in liquid preservatives containing methanol, such as PreservCyt™ solution, breaks up mucus and lyses red blood cells and inflammatory cells, without affecting the cells of interest. The liquid is then passed through a filter with an aperture covered by a membrane to concentrate and collect the cells. Debris, such as lysed blood cells and dispersed mucus, which flow through the pores of the membrane, are not collected on the membrane and are greatly reduced by the combined method of dispersion and filtering. Then, the cells collected on the membrane are transferred onto a slide. Existing filter transfer methods typically transfer cells from the membrane to the slide in a "semi-dry" environment, i.e., in an environment where a majority of the fluid has been removed from the filter assembly.

SUMMARY OF THE DISCLOSED INVENTIONS

Apparatuses and methods are disclosed herein for preparing cytological specimens on strata such as glass slides, and, more particularly, to apparatuses and methods for preparing cytological specimens in a "wet" environment using microfluidic techniques.

In one embodiment, an apparatus for processing a specimen from a fluid sample includes a first set of one or more microfluidic channels configured to deliver the sample fluid to a filter disposed on an inflatable bladder configured to transfer the specimen from the filter to a slide. The apparatus is configured to collect an approximate monolayer of particles, and includes a second set of one or more microfluidic channels configured to remove fluid flowing through the filter disposed on the inflatable bladder. The apparatus also includes, or may otherwise be coupled to, a pressure source, with a sample container connected (or connectable) to the pressure source and the first set of one or more microfluidic channels, a fluid flow gauge configured to measure a fluid flow rate through the filter, and a stain source connected to the first set of one or more microfluidic channels. The filter may include a membrane.

In another embodiment, an apparatus for processing a specimen from a fluid sample includes a first layer and a second layer. The first layer includes a first set of one or more microfluidic channels configured to deliver the sample fluid to a filter. The second layer includes a second set of one or more microfluidic channels configured to remove fluid flowing through the filter, and an inflatable bladder configured and positioned relative to the filter to transfer the specimen from the filter to a slide. The apparatus is preferably configured to collect an approximate monolayer of particles and includes a second set of one or more microfluidic channels configured to remove fluid flowing through the filter disposed on the inflatable bladder. The apparatus also includes, or may otherwise be coupled to, a pressure source, with a sample container connected (or connectable) to the pressure source and the first set of one or more microfluidic channels, a fluid flow gauge configured to measure a fluid flow rate through the filter, and a stain source connected to the first set of one or more microfluidic channels. The filter may include a membrane.

In yet another embodiment, a method of processing a specimen from a fluid sample, includes forcing the fluid sample through a set of one or more microfluidic channels and a filter, collecting the specimen on the filter, and inflating a bladder to force the filter into contact with a slide, thereby transferring the collected specimen from the filter to the stratum. Collecting the specimen on the filter includes collecting a substantial monolayer of the particles from the liquid suspension and disposing the collected particles on the slide. The method may also include forcing a stain through the set of one or more microfluidic channels and onto the collected specimen on the slide, as well as using a measured fluid flow rate to calculate a proportion of the filter that is occluded by the collected specimen. The filter may include a membrane.

Other and further aspects and embodiments of the disclosed inventions are described in the detailed description of the accompanying drawings.

BRIEF DESCRIPTION OF THE DRAWINGS

It will be appreciated that the apparatuses shown in the drawings are not necessarily drawn to scale, with emphasis instead being placed on illustrating the various aspects and features of the illustrated embodiments, in which.

DETAILED DESCRIPTION OF THE ILLUSTRATED EMBODIMENTS

Embodiments of the disclosed inventions will now be described with reference (where applicable) to the drawings. It is, however, expressly noted that the disclosed inventions are not limited to these described and/or illustrated embodiments, and that many modifications variations will apparent to the person skilled in the art without departing from the underlying scope of the disclosed inventions and equivalents thereof. It should also be appreciated that, for ease in illustration and explanation, a same reference number may used for a same or similar structure or operation in different figures and embodiments of the disclosed inventions.

Figure 1:
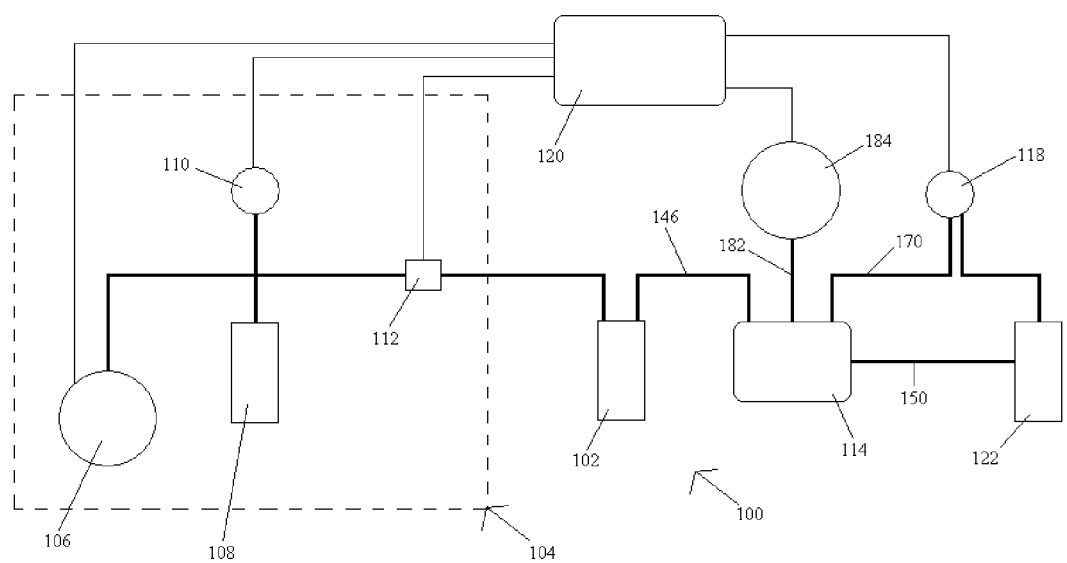
FIG. 1 is a schematic view of a microfluidic cytological specimen preparation apparatus constructed according to exemplary embodiments of the disclosed inventions.

Referring to FIG. 1, an embodiment of a microfluidic cytological specimen preparation apparatus 100 includes a sample vial 102 containing sample fluid (not shown). A pressure source 104 is connected to the sample vial 102. The pressure source includes a pump 106, a pressure vessel 108 connected thereto, a pressure gauge connected to the pressure vessel 108, and a pressure control valve 112 connected to the pressure vessel 108 and the sample vial 102. The pump 106 is configured to pressurize the pressure vessel 108. The pressure in the pressure vessel 108 can be monitored using the pressure gauge 110. A pressure control valve 112 intervening between the pressure vessel 108 and the sample vial 102 is used to modulate the pressure on the sample vial 102.

The sample vial 102 is also connected to a microfluidic circuit 114, which is configured to collect particles (not shown) suspended in the sample fluid (not shown) and to transfer the collected particles (not shown) to a slide 130 for microscope examination. The microfluidic circuit 114 is also connected to a fluid flow gauge 118, which is configured to measure a fluid flow rate through the microfluidic circuit 114.

The microfluidic cytological specimen preparation apparatus 100 also includes a computer 120, which is configured to determine, using the measured fluid flow rate through the microfluidic circuit 114 from the fluid flow gauge 118, when an approximately single cell thick specimen (not shown) has been collected in the microfluidic circuit 114. Details of the above-described determination are disclosed in provisional application Ser. No. 61/015,340, filed Dec. 20, 2007, entitled "Method for Measuring Occlusion of a Filter by Fluid Flow," which is expressly incorporated herein by reference. The computer 120 is connected to and controls the pump 106 and the pressure control valve 112. The computer 120 is connected to and receives information from the pressure gauge 110 and the fluid flow gauge 118. The flow gauge 118 is also connected to a waste container 122.

Figure 2:
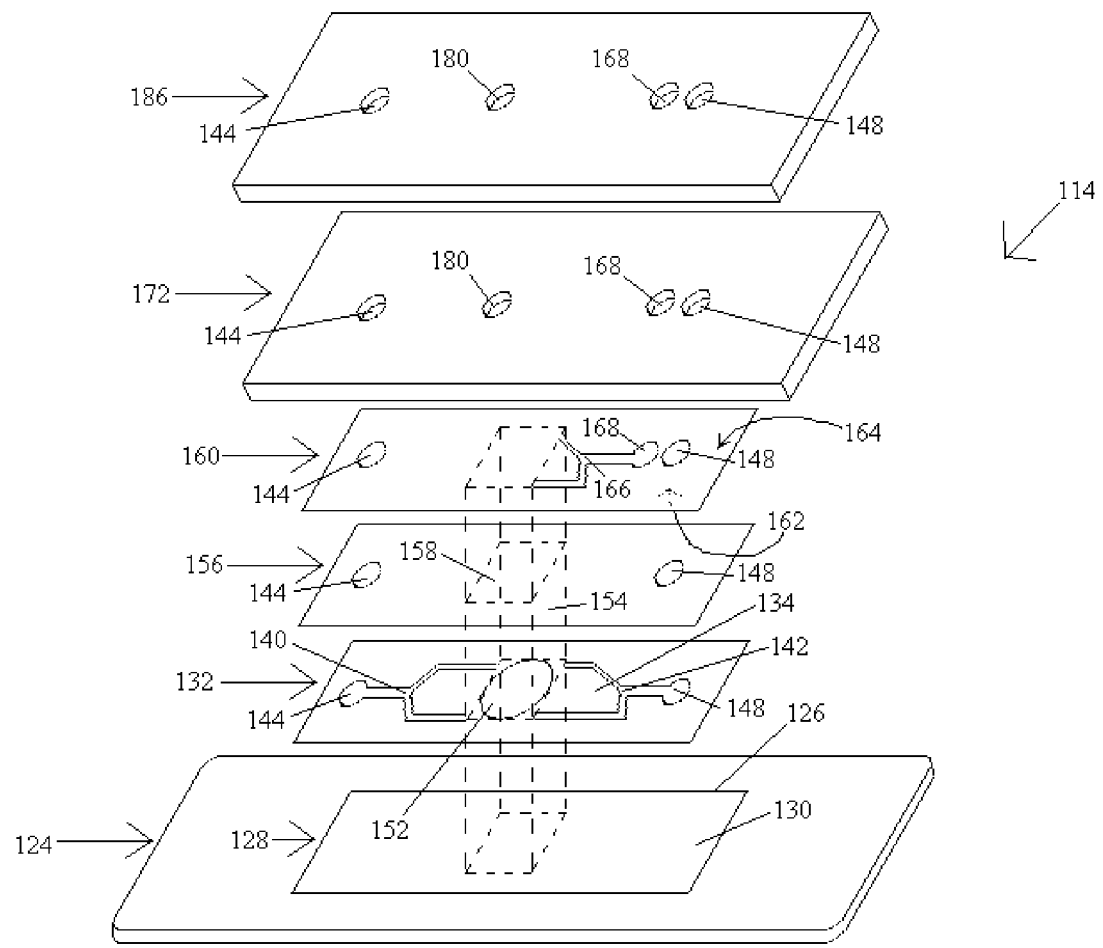
FIG. 2 is a detailed exploded perspective view of a microfluidic circuit constructed according to exemplary embodiments of the disclosed inventions.

As shown in FIG. 2, the microfluidic circuit 114 includes seven layers. Starting from the bottom, the base layer 124 supports the microfluidic circuit 114 and may be formed from metal. The base layer 124 has a depression 126 into which a slide layer fits 128. The slide layer 128 is made of a glass slide 130 onto which the specimen (not shown) will be collected.

Figure 3A:
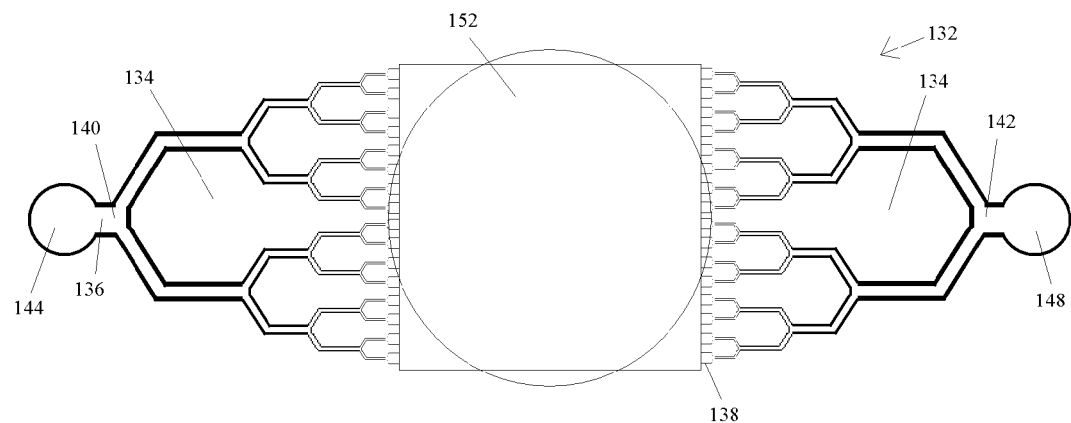
FIG. 3A is a detailed top view of a microfluidic wafer constructed according to exemplary embodiments of the disclosed inventions.

The next layer is the input layer 132 having a pattern of channels 134, which can be made of a thin sheet of polydimethylsiloxane ("PDMS") using a reverse mold of SU-8 on a silicon wafer made by standard photolithographic techniques. The pattern 134 may be a binary tree structure as shown in FIG. 3A. In this embodiment, the pattern 134 is 200 μms thick, the largest channels 136 in the pattern 134 are approximately 2 mm wide and the smallest channels 138 are 200 μms wide. The pattern 134 is first designed using computer aided design software such as DWGEditor™, and then the design is used to make a photolithographic mask which is used in turn to make a mold out of a photoresist such as SU-8. The input layer 132 includes input channels 140 and stain output channels 142.

As shown in FIGS. 1 and 2, the input channels 140 are connected through an input conduit 144 and input tubing 146 to the sample vial 102. Similarly, the stain output channels 142 are connected through a stain output conduit 148, stain output tubing 150, and a flow control valve [not shown] to the waste container 122. The input conduit 144 and output conduit 148 are both formed from openings in the layers above the input layer 132. The input tubing 146 and output tubing 150 are standard laboratory tubing.

Referring to FIGS. 2 and 3A, a circular open cavity 152 is punched into the center of the input layer 132, to create an input path 154 from the pattern of channels 134 to the next layer, the filter layer 156. The filter layer 156 includes a standard track etched membrane 158, which could be made from Mylar D, and whose perimeter is pressure sealed or bonded to adjacent layers. In alternative embodiments, the filter layer 154 comprises other apparatuses configured to collect particles in solution.

Figure 3B:
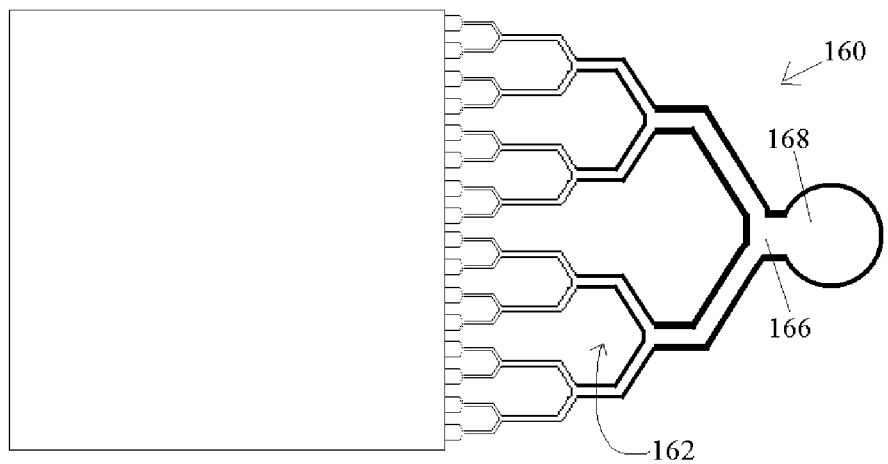
FIG. 3B is a detailed bottom view of another microfluidic wafer constructed according to exemplary embodiments of the disclosed inventions.

The next layer is the output layer 160. As shown in FIG. 3B, output layer 160 has a bottom facing surface 162 and a top facing surface 164. The bottom facing surface 162 has disposed thereon output channels 166 similar to the pattern of channels 134 in the input layer 132. The output layer 160 and output channels 166 can also be made using standard lithography techniques as described above. As shown in FIGS. 1 and 2, the output channels 166 are connected through the output conduit 168 and output tubing 170 to the waste container 122 via the fluid flow gauge 118. The top facing surface 164 is bonded to the next layer, the transfer layer 172, to form a bladder 174.

Figure 4A:
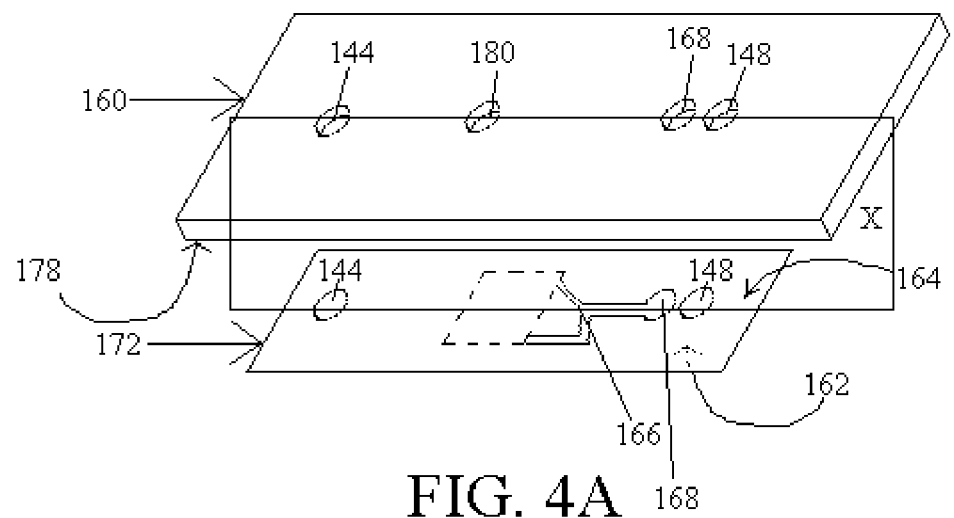
FIG. 4A is a detailed exploded perspective view of the microfluidic circuit of FIG. 2.
Figure 4B:
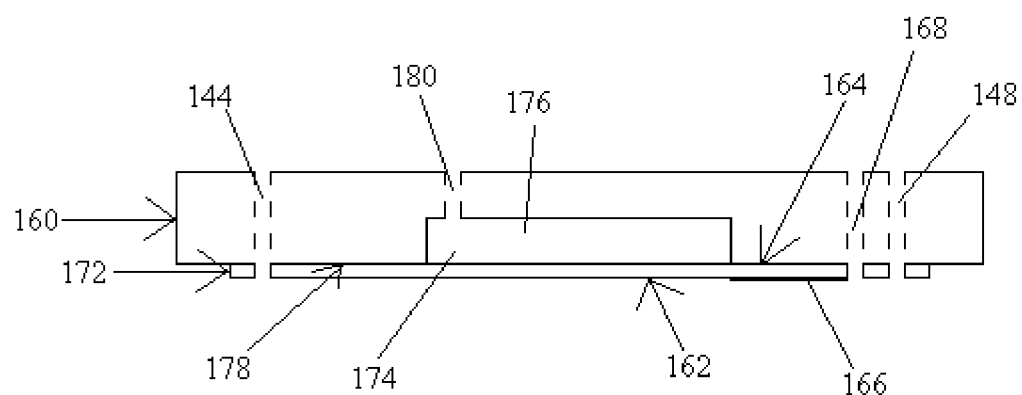
FIG. 4B is a detailed cross sectional view of the microfluidic circuit of FIG. 4A through the plane X.
Figure 5:
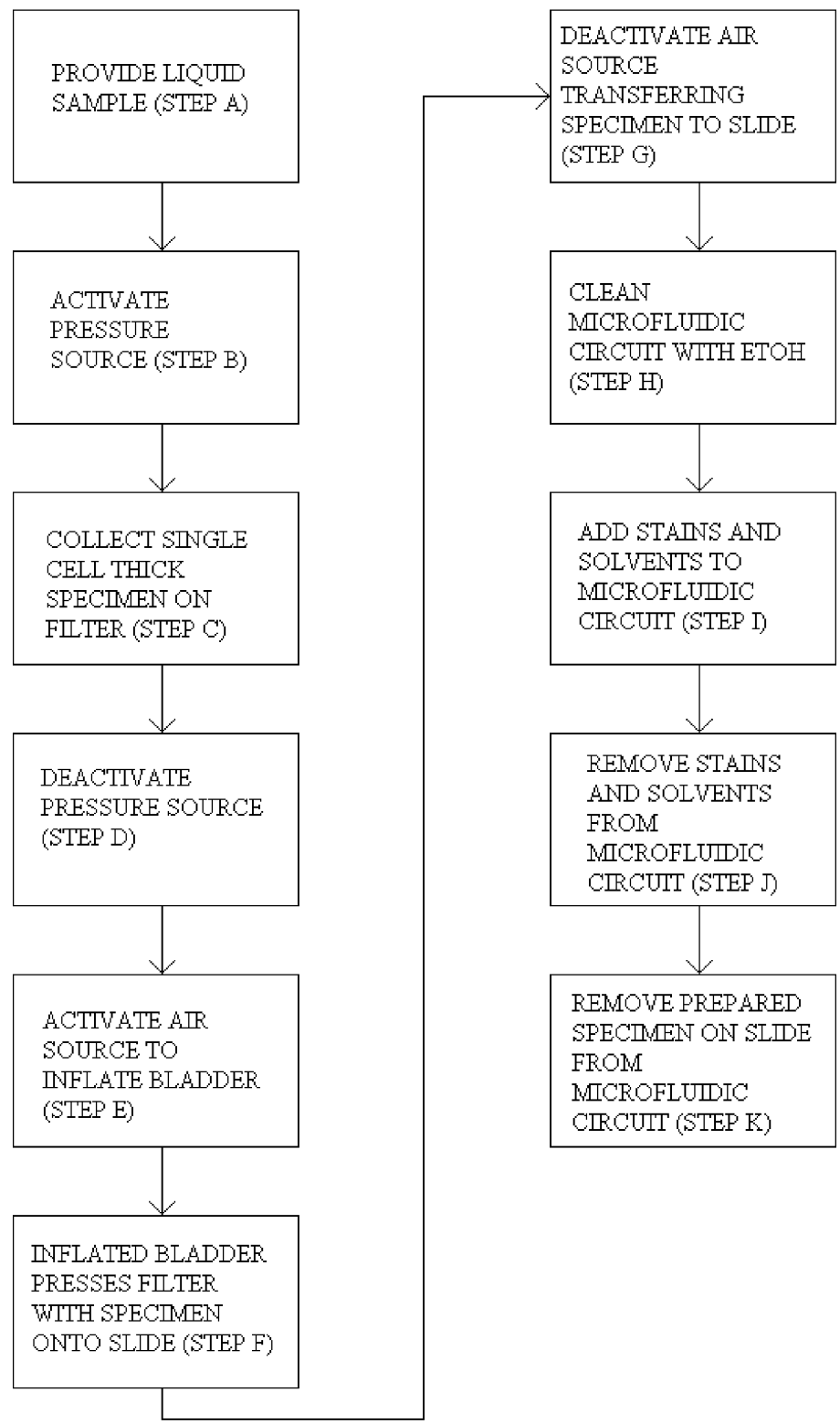
FIG. 5 is a flow chart of a specimen preparation process in accordance with exemplary embodiments of the disclosed inventions.

As shown in FIG. 4B, the transfer layer 172 has a recess 176 in its bottom surface 178. The output layer top surface 164 is bonded to the transfer layer bottom surface 178, covering the recess 176 and forming the bladder 174. As shown in FIGS. 1 and 2, the bladder 174 is connected through an air conduit 180 and air tubing 182 to the air source 184. Air tubing 182 may be 0.04 inch ID diameter Tygon™ tubing. In alternative embodiments the transfer layer 172 comprises other apparatuses configured to mechanically transfer a collected specimen from the filter layer 156 to the slide layer 128.

Referring to FIG. 2, the next and last layer is the plexiglass layer 186, which consists of a block of plexiglass with portions of the input conduit 144, the stain output conduit 148, the output conduit 168, and the air conduit 180 passing there through. The plexiglass layer 186 is bolted to the base layer 124 to hold all seven layers (124, 128, 132, 156, 160, 172, and 186) together.

FIG. 6 depicts a method of processing a specimen from a fluid sample. First a liquid sample containing sample particles is provided in the sample vial 102 (step A). The stain output path is closed and the pressure source 104 is then activated, with the pressure valve 112 is adjusted to provide sufficient pressure to achieve a desired initial flow rate of about 250 microliters per minute as measured by the fluid flow gauge 118 (step B). The liquid sample is allowed to flow through the microfluidic circuit 114 at the same pressure until the change in flow rate indicates that an approximately single cell thick specimen has collected on the membrane 158 in the filter layer 156 (approximately several minutes depending on the cell density of the sample) (step C). Then the pressure source is deactivated (step D).

Next, the air source 184 is activated and approximately 15 cubic centimeters of air is forced into the air tubing 182 to inflate the bladder 174 (step E). Inflating the bladder 174 causes it to expand along the input path 154, where the bladder 174 presses the membrane 158 with the collected specimen onto the glass slide 130 (step F). Then the air source 184 is deactivated and the air is released from the bladder 174 (step G). The elasticity of the PDMS in the transfer layer 172 and the output layer 160 that make up the bladder 174 causes the bladder 174 to deflate and contract away from the glass slide 130. During this contraction, the surface tension between the collected specimen and the glass slide 130 causes the specimen to transfer from the membrane 158 to the slide 130. The shape of the aperture designed into the input layer 132 can determine the shape of the transferred cell spot on the glass slide 130.

After the specimen has been transferred to the glass slide 130, a solution of 95% alcohol is infused into the microfluidic circuit for several minutes (step H). Next, a sequence of stains and solvents, such as the sequence used in a Sakura DRS-601 slide stainer, is introduced sequentially into the input layer 132 (step I). Each stain and solvent is introduced via a valve-controlled manifold coupling (not shown), and then it is forced out of the stain output channels by the introduction of the next stain or solvent in the sequence (step J). Then the glass slide 130 with a stained specimen attached thereto is removed from the microfluidic circuit (step K).

While the disclosed embodiments are susceptible to various modifications, and alternative forms, specific examples thereof have been shown in the drawings and are herein described in detail. It should be understood, however, that the disclosed inventions are not to be limited to the particular embodiments disclosed herein, but are to be limited only by the scope of the appended claims and their equivalents.

What is claimed is:

1. An apparatus for processing a specimen obtained from a fluid sample, comprising:
    a filter;
    a slide disposed adjacent the filter;
    a plurality of input microfluidic channels configured to deliver the fluid sample fluid to the filter, wherein the fluid sample comprises particles in a liquid suspension, and wherein the apparatus is configured to collect a specimen comprising substantially a monolayer of the particles from the liquid suspension onto the filter, each input microfluidic channel having a longitudinal axis, the longitudinal axes of the input microfluidic channels all lying in a single plane; and
    a transfer mechanism configured to transfer the specimen from the filter to the stratum slide.

2. The apparatus of claim 1, wherein the transfer mechanism comprises an inflatable bladder.

3. The apparatus of claim 2, further comprising an output microfluidic channel configured to remove fluid flowing through the filter.

4. The apparatus of claim 3, wherein the output microfluidic channel is disposed on the inflatable bladder.

5. The apparatus of claim 1, further comprising
    a fluid sample container connected or connectable to a pressure source and to the plurality of input microfluidic channels, and
    a fluid flow gauge configured to measure a fluid flow rate through the filter.

6. The apparatus of claim 1, further comprising a stain source connected to the plurality of input microfluidic channels.

7. An apparatus for processing a specimen from a fluid sample, comprising:
    a filter;
    a stratum disposed adjacent the filter;
    a first layer comprising a plurality of input microfluidic channels configured to deliver the fluid sample to the filter, each input microfluidic channel having a longitudinal axis, the longitudinal axes of the input microfluidic channels all lying in a single plane;
    a second layer comprising an output microfluidic channel configured to remove fluid flowing through the filter; and
    a transfer mechanism configured to transfer the specimen from the filter to the stratum.

8. The apparatus of claim 7, wherein the transfer mechanism comprises an inflatable bladder.

9. The apparatus of claim 8, wherein the sample comprises particles in a liquid suspension, and the apparatus is configured to collect a spatial distribution of the particles from the liquid suspension and disposes the collected particles on the stratum, the spatial distribution comprising substantially a monolayer, the stratum comprising a slide.

10. The apparatus of claim 8, wherein the output microfluidic channel is disposed on the inflatable bladder.

11. The apparatus of claim 7, further comprising
    a sample container connected or connectable to a pressure source and the plurality of input microfluidic channels,
    a fluid flow gauge configured to measure a fluid flow rate through the filter, and
    a stain source connected to the plurality of input microfluidic channels.

12. An apparatus for processing a specimen obtained from a fluid sample, comprising:
    a plurality of input microfluidic channels configured to deliver a sample fluid to a filter disposed adjacent thereto, each input microfluidic channel having a longitudinal axis, the longitudinal axes of the input microfluidic channels all lying in a single plane, wherein the filter is configured to collect thereon a specimen comprising substantially a monolayer of particles from the fluid sample; and
    a transfer mechanism configured to transfer the collected specimen from the filter to a slide disposed adjacent thereto.

13. The apparatus of claim 12, wherein the transfer mechanism comprises an inflatable bladder.

14. The apparatus of claim 13, further comprising an output microfluidic channel configured to remove fluid flowing through the filter.

15. The apparatus of claim 14, wherein the output microfluidic channel is disposed on the inflatable bladder.

* * * * *

UNITED STATES PATENT AND TRADEMARK OFFICE
CERTIFICATE OF CORRECTION

| | | |
|---|---|---|
| PATENT NO. | : 8,460,619 B2 | Page 1 of 1 |
| APPLICATION NO. | : 12/574554 | |
| DATED | : June 11, 2013 | |
| INVENTOR(S) | : Howard B. Kaufman et al. | |

It is certified that error appears in the above-identified patent and that said Letters Patent is hereby corrected as shown below:

In the Claims:

At Column 5, Claim 1, line 60, "to the stratum slide" should read:

-- to the slide --

Signed and Sealed this
Twenty-second Day of April, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,460,619 B2 | Page 1 of 1 |
| APPLICATION NO. | : 12/574554 | |
| DATED | : June 11, 2013 | |
| INVENTOR(S) | : Kaufman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 519 days.

Signed and Sealed this
Thirtieth Day of September, 2014

Michelle K. Lee
*Deputy Director of the United States Patent and Trademark Office*